United States Patent [19]

Kato et al.

[11] Patent Number: 4,588,494
[45] Date of Patent: May 13, 1986

[54] OXYGEN SENSOR

[75] Inventors: Nobuhide Kato, Aichi; Takao Murase, Konan, both of Japan

[73] Assignee: NGK Insulators, Ltd., Japan

[21] Appl. No.: 709,802

[22] Filed: Mar. 8, 1985

[30] Foreign Application Priority Data

Mar. 16, 1984 [JP] Japan .............................. 59-38406[U]

[51] Int. Cl.$^4$ ....................... G01N 27/04; G01N 27/58
[52] U.S. Cl. ....................................... 204/426; 338/34
[58] Field of Search ................ 204/425, 426, 1 S, 428; 338/34; 339/217 S

[56] References Cited

U.S. PATENT DOCUMENTS

| | | | |
|---|---|---|---|
| 3,311,866 | 3/1967 | Williamson | 339/217 S |
| 3,351,891 | 11/1967 | Schneck | 339/217 S X |
| 3,630,874 | 12/1971 | Olette et al. | 204/1 T X |
| 4,111,778 | 9/1978 | Davis et al. | 204/428 |
| 4,309,897 | 1/1982 | Springer et al. | 338/34 X |
| 4,334,974 | 6/1982 | Muller et al. | 204/425 |
| 4,364,226 | 12/1982 | Croset et al. | 60/276 |
| 4,441,982 | 4/1984 | Ueno | 204/426 |
| 4,453,397 | 6/1984 | Ohta et al. | 338/34 X |
| 4,505,807 | 3/1985 | Yamada | 204/425 |

Primary Examiner—G. L. Kaplan
Attorney, Agent, or Firm—Parkhurst & Oliff

[57] ABSTRACT

An oxygen sensor including an elongate planar oxygen sensing element which has an oxygen detecting portion adjacent to one longitudinal end thereof. The detecting portion is exposed to a measurement gas to determine an oxygen concentration of the measurement gas. The sensing element is electrically connected to at least one external device through conductor members. An electrical terminal portion is formed on the sensing element, adjacent to the other longitudinal end thereof. The terminal portion has at least one pair of electrical contacts which are disposed adjacent to corresponding connectors for direct contact therewith.

22 Claims, 10 Drawing Figures

OXYGEN SENSOR

BACKGROUND OF THE INVENTION

The present invention relates generally to an oxygen sensor for detecting the oxygen concentration of a measurement gas, especially an exhaust gas produced by an internal combustion engine. More particularly, the invention is concerned with such an oxygen sensor which uses an elongate planar sensing element having an oxygen detecting portion at its one end, and which is simple in construction and easy to manufacture and assemble.

There has been known an oxygen sensor which detects or determines the oxygen concentration of an exhaust gas emitted from internal combustion engines, for the purpose of controlling the combustion or fuel burning condition of the engine according to signals produced by the oxygen sensor, and thereby purifying the exhaust gas and saving the fuel consumption of the engine. An example of such oxygen sensors uses a sensing element which comprises a body of oxygen-ion conductive solid electrolyte such as zirconium oxide doped with calcium oxide or yttrium oxide, and further comprises suitable electrodes disposed on opposite surfaces of the solid electrolyte body. In this oxygen sensor, one of the electrodes is exposed to a reference gas while the other electrode is exposed to the exhaust gas. In operation, the oxygen sensor produces an output signal which represents an electromotive force induced between the two electrodes according to the principle of an oxygen concentration cell. In recent years, there has been an increasing tendency to use an elongate planar sensing element rather than a conventionally used tubular sensing element, in view of ease of manufacture and structural simplicity of the sensor. Such an elongate planar sensing element has, at its one end, a detecting portion to be exposed to an exhaust gas or other measurement gas.

In an oxygen sensor discussed above, the output of the sensor is obtained as an electric signal which represents the oxygen partial pressure of the measurement gas detected by the detecting portion. This electric signal should be fed to an external device. For this purpose, electrical leads of the electrodes should be electrically connected to external conductor members or lead wires which are inserted into the housing of the oxygen sensor. Since the sensing element carrying the leads is of elongate planar configuration, it has been impossible to connect the external lead wires directly to the leads on the sensing element. Accordingly, it has been a common practice to use auxiliary leads which are extensions of the leads formed on the sensing element. These auxiliary leads are connected to the external lead wires as with suitable calking actions, at a position away from the sensing element. However, the use of such auxiliary leads complicates the electrical arrangement of the sensor, and therefore results in reduced efficiency of manufacture and assembly of the sensor. Further, the procedure to make electrical connections between the auxiliary leads and the external lead wires is difficult and cumbersome. In addition, the reliability of the electrical connections is not completely satisfactory.

It is also noted that an oxygen sensor of the aforementioned type is provided with an electrical heater which is incorporated within the sensing element in order to heat the detecting portion for reliable and accurate operation of the detecting portion. To supply power to such a heater, additional external lead wires should be connected to the leads of the heater. In this case, too, the same problems as pointed out above are encountered. In summary, a plurality of conductor members, i.e., plural pairs of lead wires should be connected to the corresponding plural pairs of electrical leads of the sensing element, within the sensor housing, to obtain an output signal from the detecting portion of the sensing element and to actuate the heater in the element. Considering the need that the oxygen sensor be constructed as compact as possible, it is an extremely difficult procedure to make electrical connections of the signal leads and the heater leads to the corresponding external wires, at not a few locations within the compact assembly of the oxygen sensor. Even if these electrical connections are not impossible, the provisions for the connections necessarily complicate the overall structure of the oxygen sensor.

SUMMARY OF THE INVENTION

It is therefore an object of the present invention to provide an oxygen sensor which has relatively simple means for easy and quick electrical connections associated with its sensing element, and which is easy to manufacture and assemble.

According to the invention, there is provided an oxygen sensor including an elongate planar sensing element which has an oxygen detecting portion adjacent to one longitudinal end thereof, the detecting portion being exposed to a measurement gas to determine an oxygen concentration of the measurement gas, the sensing element is electrically connected to at least one external device through conductor members, characterized in that electrical terminal means is formed on the sensing element, adjacent to the other longitudinal end thereof, the terminal means including at least one pair of electrical contacts, and in that connector means is disposed adjacent to the electrical terminal means, the connector means including connectors which are electrically connected to the conductor members and are held in direct contact with the at least one pair of electrical contacts, respectively.

According to one embodiment of the invention, the electrical terminal means of the sensing element takes the form of a plug, while the connector means takes the form of a receptacle in which the plug is inserted for pressed contact of said at least one pair of electrical contacts with the connectors.

According to an alternative embodiment of the invention, the electrical terminal means takes the form of a receptacle, while the connector means takes the form of a plug which is inserted in the receptacle for pressed contact of the connectors with said at least one pair of electrical contacts.

According to another embodiment of the invention, said at least one pair of electrical contacts consists of an output signal contact and an earth contact, and the conductor members include a metallic covering member accommodating therein the sensing element. In this case, the output signal contact is connected to the external device through the corresponding one of the connectors and through one of the conductor members, while on the other hand the earth contact is grounded through the corresponding one of the connectors and through the metallic covering member.

In accordance with a further embodiment of the invention, said at least one pair of electrical contacts comprises end portions of at least one pair of electrical leads formed on the sensing element. These end portions of the electrical leads are exposed adjacent to said other longitudinal end of the sensing element.

In one form of the above embodiment, said at least one pair of electrical leads comprises a pair of leads connected to a pair of electrodes disposed in said oxygen detecting portion of the sensing element, one of this pair of electrodes being exposed to the measurement gas.

In another form of the above embodiment, the sensing element comprises an electrical heater incorporated therein to heat said oxygen detecting portion thereof, and said at least one pair of electrical leads comprises a pair of leads connected to the electrical heater to apply power thereto.

In accordance with a further embodiment of the invention, said at least one pair of electrical contacts are exposed adjacent to said other longitudinal end of the planar sensing element, each of the electrical contacts being raised above a surface of the planar sensing element. In this embodiment, said at least one pair of electrical contacts may comprise a first pair of electrical contacts electrically connected to a pair of electrodes disposed in the oxygen detecting portion of the sensing element, and a second pair of electrical contacts electrically connected to an electrical heater incorporated in the sensing element to heat the oxygen detecting portion. The first pair of electrical contacts consists of end portions of electrical leads extending from the electrodes, respectively, and the second pair of electrical contacts consists of end portions of electrical leads extending from the electrical heater. Each of the end portions of the electrical leads is raised above a surface of the sensing element.

In one advantageous arrangement of the above embodiment, the end portions of the electrical leads extending from the pair of electrodes are formed on one of opposite surfaces of the sensing element perpendicular to the direction of thickness thereof, while the end portions of the electrical leads extending from the electrical heater are formed on the other of the opposite surfaces of the sensing element.

In another advantageous arrangement, the end portions of the electrical leads of the electrodes are formed substantially in the same plane perpendicular to the direction of thickness of the sensing element. Similarly, the end portions of the electrical leads of the electrical heater may be formed substantially in the same plane perpendicular to the direction of thickness of the sensing element.

In an alternative arrangement, the end portions of the electrical leads extending from the electrodes are formed in different planes perpendicular to the direction of thickness of the sensing element.

The oxygen sensor may further comprise an electrically insulating member in which the connectors are fixedly supported for electrical contact with said at least one pair of electrical contacts. In this case, an end portion of said sensing element on the side of said other longitudinal end thereof is inserted into the insulating member for electrical contact of the electrical contacts with the connectors. Each of the connectors may have a contact lug which is held in resiliently pressed contact with the corresponding one of the electrical contacts.

The oxygen detecting portion of the sensing element may be made of a solid electrolyte material consisting substantially of zirconia ceramics, and is operated to determine the oxygen concentration of the measurement gas according to the principle of an oxygen concentration cell. Alternatively, the oxygen detecting portion of the sensing element may be made of an oxide semiconductor the electrical resistance of which is varied as a function of an oxygen partial pressure of the measurement gas.

BRIEF DESCRIPTION OF THE DRAWING

These and other objects, features and advantages of this invention will become more apparent from reading the following detailed description of illustrative embodiments taken in connection with the accompanying drawings, in which.

DETAILED DESCRIPTION OF THE PREFERRED EMBODIMENTS

To further clarify the present invention, preferred embodiments thereof will be described in detail, referring to the accompanying drawing.

Figure 1:
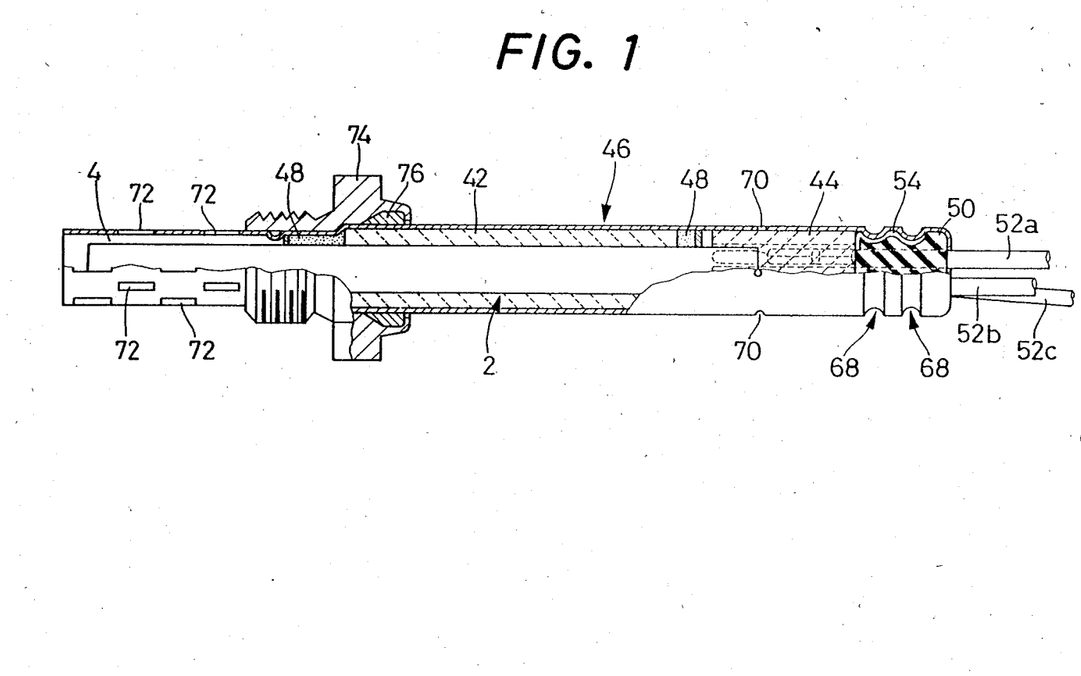
FIG. 1 is a fragmentary view partly in cross section of one embodiment of an oxygen sensor of the present invention.

There is shown in FIG. 1 an oxygen sensor embodying the invention, comprising an oxygen sensing element 2 consisting of an elongate planar laminar structure which is generally rectangular in transverse cross section and which is made of solid electrolyte materials, consisting substantially of zirconia ceramics. As indicated also in FIG. 2, the oxygen sensing element 2 has an oxygen detecting portion 4 at its inner or first end.

Described in greater detail with reference to FIGS. 2 through 5, the sensing element 2 comprises an elongate planar solid electrolyte body 6 consisting substantially of zirconia ceramics, and a porous inner electrode 8 made of platinum or other suitable material which is formed by printing on an area of the outer surface of the solid electrolyte body 6 adjacent to one end thereof corresponding to the oxygen detecting portion 4. On the surface of the solid electrolyte body 6 on which the inner electrode 8 is printed, there are laminated a zirconia frame 10 and an oxygen sensing layer 12, which also consist substantially of zirconia ceramics, such that the inner electrode 8 is interposed between the solid electrolyte body 6 and the zirconia frame 10 and such that the sensing layer 12 is disposed on the zirconia frame 10. A porous outer electrode 14 made of the same material as the inner electrode 8 is printed on the sensing layer 12. The outer electrode 14 is protected, except at its sensing portion, by a protective layer 16 which is made of the same material as the sensing layer 12.

Figure 2:
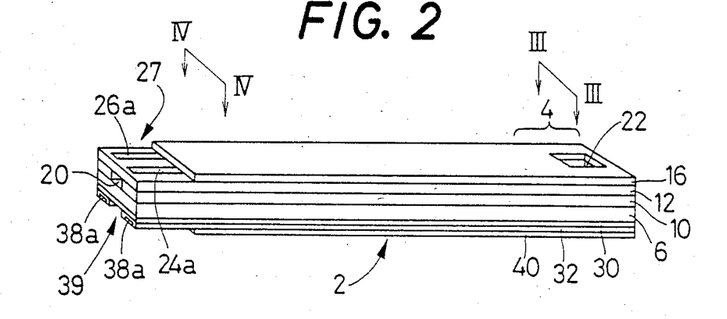
FIG. 2 is a perspective view of an example of an oxygen sensing element used in the oxygen sensor according to FIG. 1.
Figure 3:
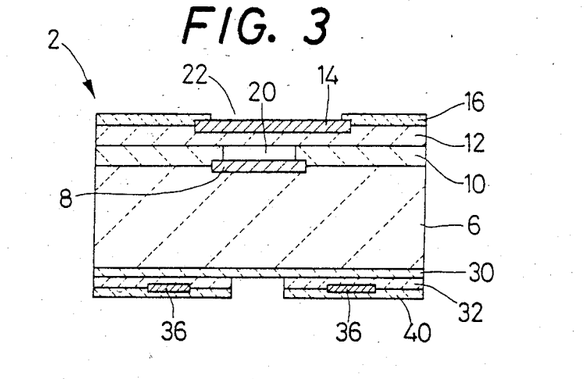
FIGS. 3 and 4 are cross sectional views taken along lines III—III and IV—IV of FIG. 2; respectively.
Figure 4:
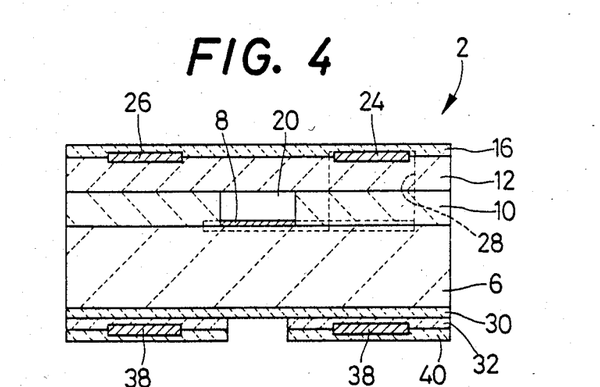
Figure 5:
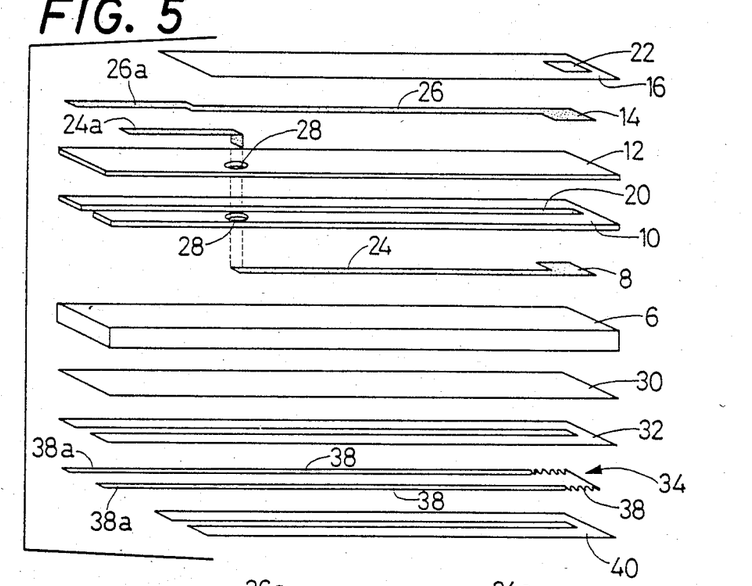
FIG. 5 is an exploded view of the oxygen sensing element of FIG. 2.

The zirconia frame 10 has an elongate rectangular cutout formed along the length thereof in its widthwise central region. This cutout cooperates with the solid electrolyte body 6 and the sensing layer 12 to define a reference-gas passage 20 which is closed at its one end near the end of the zirconia frame 10 corresponding to the detecting portion 4. The reference-gas passage 20 is open to the ambient air at its other end. The inner electrode 8 is disposed adjacent to the closed end part of the passage 20 so that the electrode 8 is exposed to the atmosphere in the passage 20. In the meantime, the outer electrode 14 which is printed on the side of the sensing layer 12 opposite to the zirconia frame 10, is located substantially in alignment with the inner electrode 8, so that the electrode 14 is exposed to a measurement gas outside the sensing element 2, via a window 22 formed in the protective layer 16. The inner and outer electrodes 8 and 14 are provided with electrical leads 24 and 26, respectively, which extend therefrom along the length of the sensing element 2 toward its outer or second end, for electrical connection of the electrodes 8, 14. The entire length of the electrical lead 26 of the outer electrode 14 is formed on the outer surface of the sensing element 12, while the electrical lead 24 of the inner electrode 8 is partially formed on the surface of the solid electrolyte body 6. Stated more specifically, the zirconia frame 10 and the sensing layer 12 have holes 28 formed through the thickness thereof. The lead 24 is turned, at its intermediate portion, at right angles to the surface of the solid electrolyte body 6 toward the lead 26, so that its end portion 24a remote from the inner electrode 8 is disposed in substantially the same plane as the corresponding end portion 26a of the lead 26. This plane is substantially perpendicular to the direction of thickness of the sensing element 2, as shown in FIG. 2. The electrical leads 24, 26 extend, in parallel with each other, from the respective electrodes 8, 14 between the sensing and protective layers 12, 16 toward the second end of the sensing element 2 and are exposed at 24a, 26a, at the second end portion of the sensing element 2 as clearly shown in FIG. 2. These end portions 24a, 26a of the leads 24, 26 serve as electrical contacts which constitute first electrical terminal means (terminal portion) 27.

In the above-described arrangement of the oxygen sensing element 2, an external space communicating with the window 22 at the detecting portion 4 is kept in fluid-tight condition with respect to the reference-gas passage 20 defined by the zirconia frame 10, solid electrolyte body 6 and sensing layer 12. The inner electrode 8 is exposed to a reference gas, such as the ambient air, in the passage 20, while the outer electrode 14 is exposed to an external measurement gas introduced through the window 22, as previously indicated. With these gases contacting the inner and outer electrodes 8, 14, respectively, an electromotive force is induced, according to the principle of an oxygen concentration cell, between the inner and outer electrodes 8, 14 due to a difference in oxygen partial pressure between the two gases, whereby an output signal indicative of such an electromotive force is obtained through the respective leads 24, 26.

In this illustrated embodiment, the ambient air is introduced as a reference gas in the reference-gas passage 20 formed in the zirconia frame 10, while an exhaust gas emitted from an internal combustion engine such as an automotive vehicle engine is introduced, as a measurement gas, toward the outer electrode 14 through the window 22 in the protective layer 16. Namely, the oxygen concentration of the measurement gas (exhaust gas) is measured by using the ambient air as a reference gas. The output signal representative of the oxygen concentration is obtained through the electrical leads 24, 26, more precisely, at the end portion 24a of the lead 24, which serves as an output signal contact. The end portion 26a of the lead 26 serves as an earth (or ground) contact which cooperates with the output signal contact to constitute the first terminal means 27 that is exposed on one side of the second end portion of the sensing element 2.

On the side of the solid electrolyte body 6 opposite to the side on which the inner electrode 8 is printed, there are disposed an alumina insulating layer 30, a zirconia insulating layer 32, and an electrical heater 34 which comprises a heating element 36 and two leads 38, 38 connected thereto. The heating element 36 is located in alignment with the oxygen detecting portion 4 of the sensing element 2, and a pair of electrical leads 38, 38 extend from the heating element 36 along the length of the sensing element 2 toward its second end portion, so that power is applied to the heating element 36 through these leads 38 to heat the detecting portion 4 of the sensing element 2 upon energization of the heating element 36. This pair of electrical leads 38, 38 are protected, except at their end portions 38a, 38a, by a protective layer 40 made of zirconia ceramics, against exposure thereof to the exhaust gas. In other words, the end portions 38a, 38a are exposed at the second end portion of the sensing element 2, and serve as electrical contacts which constitute second electrical terminal means (terminal portion) 39 disposed on the side opposite to the first electrical terminal means 27 for the inner and outer electrodes 8, 14.

The oxygen sensing element 2 having the oxygen detecting portion 4 at its first or inner end is supported at its intermediate portion by a first ceramic insulating member 42, and at its second end portion by a second ceramic insulating member 44. These first and second ceramic insulating members 42, 44 are accommodated in a cylindrical metallic protective covering 46, and fixed therein by fillers 48, 48 made of cement or other suitable material, which are provided at opposite longitudinal ends of the first ceramic insulating member 42. The fillers 48, 48 separate the interior of the protective covering 46 into plural spaces in mutually fluid-tight condition. The sensing element 2 is positioned such that its oxygen detecting portion 4 is disposed in the space formed in one end portion (left-hand side end portion as seen in FIG. 1) of the protective covering 46 corresponding to the first or inner end portion of the sensing element 2, and such that the reference-gas passage 20 is open in the space formed in the second or outer end portion (right-hand side end portion as viewed in FIG. 1) of the protective covering 46.

A rubber plug 50 is press-fitted in the second end portion of the protective covering 46. Electrically conductive members in the form of lead wires 52a, 52b and 52c extend through the rubber plug 50 into the second ceramic insulating member 44, for electrical connection thereof to the lead 24 of the inner electrode 8, and the leads 38 of the heater 34, respectively. Further, the rubber plug 50 holds an earth lead 54 in contact with the inner surface of the second end portion of the protective covering 46. This earth lead 54 also extends into the second insulating member 44 for electrical connection to the lead 26 of the outer electrode 14. Thus, the exposed end portions 24a, 26a of the leads 24, 26 and the exposed end portions 38a, 38a of the leads 38, 38, which are disposed on the opposite sides of the second end portion of the sensing element 2, are electrically connected within the second ceramic insulating member 44 to the lead wire 52a, earth lead 54, lead wire 52b and lead wire 52c, respectively.

Figure 6:
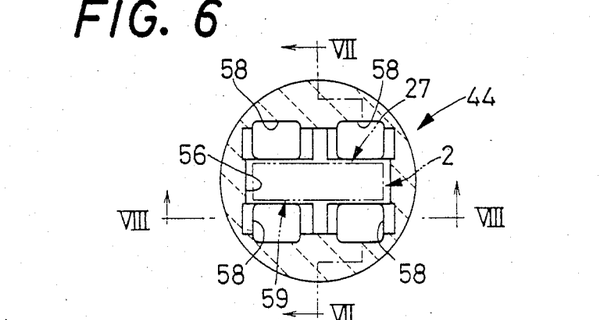
FIG. 6 is a transverse cross sectional view of an example of a ceramic insulator used in the oxygen sensor of FIG. 1 for electrical connection of its sensing element.
Figure 7:
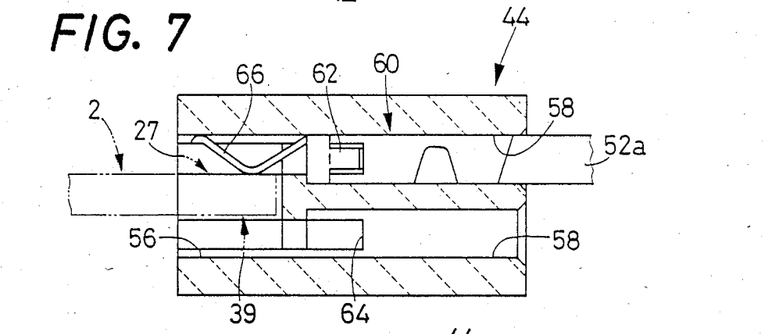
FIGS. 7 and 8 are views in cross section taken along lines VII—VII and VIII—VIII of FIG. 6, respectively.
Figure 8:
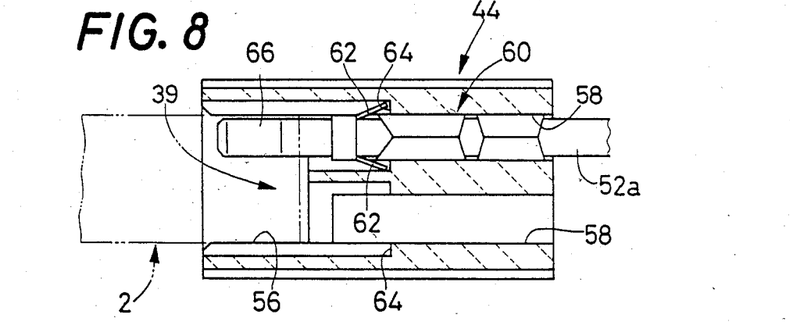

Stated more particularly referring to FIGS. 6, 7 and 8, the second ceramic insulating member 44 is a generally cylindrical member which has, on one side thereof, a recess 56 in which there is inserted the second end portion of the sensing element 2 which carries the first and second electrical terminal means 27, 39. As most clearly indicated in FIG. 6, the second ceramic insulating member 44 further has, on the other side, four lead-wire holes 58 into which the end portions of the lead wires 52a, 52b, 52c and earth lead 54 are inserted. These four lead-wire holes 58 are disposed such that the extension lines of the two holes 58, 58 are aligned with the end portions 24a, 26a of the leads 24, 26, and those of the remaining two holes 58, 58 are aligned with the end portions 38a, 38a of the leads 38, 38 on the opposite side of the sensing element 2. The four lead-wire holes 58 communicate with the recess 56 so that the lead wires 52a, 52b, 52c and earth lead 54 may be electrically coupled to the respective end portions, i.e. electrical contacts 24a, 38a, 26a of the leads 24, 38, 26 in the manner which will be described in detail.

Each of the lead wires 52a, 52b, 52c and earth lead 54 is provided at its end with a metallic connector 60 of a spring or resilient material fixed thereto by calking. In the interest of brevity and simplification, only the metallic connector 60 of the lead wire 52a to be connected to the inner electrode lead 24 is illustrated in FIGS. 7 and 8. For electrical connection of the lead wire 52a to the lead 24, for example, the end portion of the lead wire 52a with the connector 60 fixed thereto is first inserted through the corresponding wire-lead hole 58, until the end of the connector 60 reaches the end portion 24a of the lead 24. In this manner, the connectors 60 are located respectively in alignment with the end portions 24a, 26a (first electrical terminal means 27) of the electrode leads 24, 26, and the end portions 38a, 38a (second electrical terminal means 39) of the heater leads 38, 38.

As most clearly shown in FIG. 8, each of the metallic connectors 60 has two latching lugs 62 which abut on a shoulder 64 formed at the inner end of the lead-wire hole 58, whereby the connector 60 once inserted into the insulating member 44 will not be moved back away from the sensing element 2. Further, each metallic connector 60 is provided, at its end, with a contact lug 66 which extends generally longitudinally of the lead-wire hole 58 into the recess 56. The contact lug 66 is bent in the form of letter "V", so that the bottom of the V-shape is held in resiliently pressed contact with the exposed end portion 24a, 26a, 38a, 38a of the corresponding lead 24, 26, 38, 38, as shown in FIG. 7. Thus, the metallic connector 60 of each lead wire or lead 52a, 52b, 52c, 54 is electrically connected to the corresponding lead 24, 38, 38, 26.

As previously stated, the exposed end portions 24a and 26a of the leads 24 and 26 serve as a pair of electrical contacts of the first electrical terminal means 27 on one side of the second end portion of the sensing element 2, while the exposed end portions 38a, 38a of the leads 38, 38 serve as a pair of electrical contacts of the second electrical terminal means 39 on the opposite side of the second end portion of the sensing element 2. When the second end portion of the sensing element 2 is inserted into the recess 56 in the second insulating member 44, the two pairs of electrical contacts 24a, 26a, 38a, 38a are brought into pressed contact with the contact lugs 66 of the connectors 60 of the respective lead wires 52a, 52b, 52c and earth lead 54.

The earth lead 54 which is electrically connected to the lead 26 of the outer electrode 14 via the connector 60, consists for example of a bare wire which is positioned between the outer surface of the rubber plug 50 and the corresponding inner surface of the metallic protective covering 46, as depicted in FIG. 1. In this way, the earth lead 54 is electrically connected to the metallic protective covering 46 which is electrically connected to a metallic housing 74, whereby the earth lead 54 is grounded.

The end portion of the protective covering 46 in which the rubber plug 50 is accommodated, is compressed or calked radially inwardly against the surface of the rubber plug 50, at two axially spaced-apart positions. As a result, two radially inwardly indented parts 68 are formed on the end portion of the protective covering 46. These indented parts 68 compress the rubber plug 50 in the radially inward direction, thereby retaining the lead wires 52a, 52b and 52c firmly in the rubber plug 50, and preventing vibrational or rattling movements of these lead wires which would otherwise be transmitted to the associated components within the oxygen sensor, particularly to the electrical connections which have been described hitherto.

The second ceramic insulating member 44 is retained in position by the sensing element 2 partly inserted therein, and by the rubber plug 50. Since the open end of the protective covering 46 is gas-tightly closed by the rubber plug 50, the cylindrical wall of the protective covering 46 has air-inlet apertures 70 through which the reference-gas passage 20 communicates with the ambient air outside the protective covering 46.

As shown in FIG. 1, the protective covering 46 has a small-diameter end portion opposite to its end portion in which the rubber plug 50 is press-fitted. This small-diameter end portion is located in a fluid conduit such as an exhaust pipe of a vehicle through which a measurement gas such as an exhaust gas flows. The first end portion, that is, the oxygen detecting portion 4 of the sensing element 2 is disposed in the small-diameter end portion of the protective covering 46, so that the detecting portion 4 is exposed to the measurement gas which is introduced through the plurality openings 72 formed through the wall of the small-diameter end portion of the protective covering 46. The protective covering 46 extends through the previously indicated metallic housing 74 so that the metallic housing 74 supports the protective covering 46 at a portion thereof adjacent to the small-diameter end portion. The metallic housing 74 is threaded to the fluid conduit such that the small-diameter end portion of the protective covering 46 is disposed within the fluid conduit with fluid tightness between the protective covering 46 and the fluid conduit. Reference numeral 76 designates a metallic sealing ring which maintains fluid tightness between the metallic housing 74 and the protective covering 46.

In the oxygen sensor constructed as described heretofore, the inner electrode 8 disposed at the detecting portion 4 of the sensing element 2 is exposed to the ambient air in the reference-gas passage 20, which is introduced through the air-inlet apertures 70. In the meantime, the outer electrode 14 also disposed at the detecting portion 4 is exposed to the measurement gas, e.g., engine exhaust gas flowing through the exhaust pipe, which is introduced through the openings 72 and the window 22. In this arrangement, an output electrical signal indicative of the oxygen concentration of the measurement gas is obtained between the lead wire 52a connected to the inner electrode 8, and the earth lead 54 connected to the outer electrode 14.

As is apparent from the foregoing description, the exposed end portions 24a, 38a, 38a, 26a of the leads 24, 38, 38, 26 are electrically connected to the lead wires 52a, 52b, 52c and earth lead 54, by inserting the second end portion of the sensing element 2 into the recess 56 and thereby bringing the exposed end portions 24a, 38a, 38a, 26a into direct contact with the contact lugs 66 of the corresponding connectors 66.

Described differently, the mere insertion of the second end portion of the sensing element 2 between the two pairs of connectors 60 in the insulating member 44 will complete the required electrical connections of the sensing element 2. In this sense, it is considered that the exposed end portions 24a, 26a, 38a, 38a serve as male connectors while the corresponding four connectors 60 (more precisely, their contact lugs 66) serve as female connectors. Namely, the second end portion of the sensing element 2 having the first and second electrical terminal means 27, 39 is considered as a plug, while the four connectors 60 supported by the second ceramic insulating member 44 is considered as a receptacle in which the plug is inserted for pressed contact of the two pairs of electrical contacts 24a, 26a, 38a, 38a. This male-and-female or plug-and-receptacle type arrangement facilitates electrical connection of the leads 24, 38, 38, 26 to the lead wires 52a, 52b, 52c and earth lead 54, and simplifies the construction and assembly of the oxygen sensor to a considerably appreciable extent.

In the present embodiment, the electrical heater 34 is provided integrally in the sensing element 2, with their leads 38, 38 exposed at their end portions 38a, 38a as the second electrical terminal means 39 as previously described. In this connection, it is important to note that the above indicated plug-and-receptacle arrangement permits easy electrical connection of these heater leads 38, 38 to the power supply lead wires 52b, 52c, simultaneously with the electrical connection of the electrode leads 24, 26. Thus, the plural leads provided within the oxygen sensor may be electrically connected at one time by a simple insertion of the second end portion of the sensing element 2 into the second ceramic insulating member 44. This means that the advantage of the instant arrangement in terms of electrical connection, assembling and attachment of the oxygen sensor will be more appreciated as the number of electrical leads provided in the sensor is increased.

The electrical heater 34 incorporated in the sensing element 2 heats the detecting portion 4 to keep its operating temperature above a lower limit, thereby reducing the rise time of the oxygen sensor before the measurement gas temperature rises beyond the lower limit, for example, immediately after the start of a cold vehicle engine. Namely, the heater 34 assures relatively high stability of detecting the oxygen concentration of a measurement gas even while the temperature of the gas is not sufficiently high.

Figure 9:
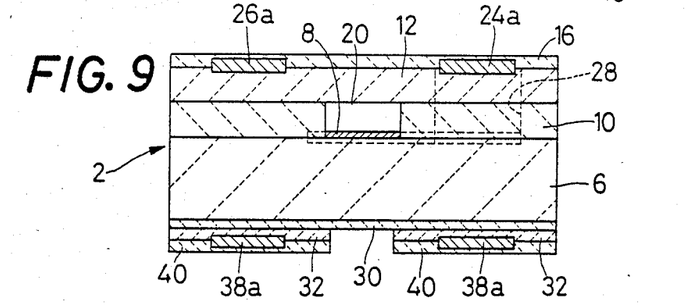
FIG. 9 is a transverse cross sectional view showing electrical terminal portions of the sensing element at which electrical leads are exposed at their end portions.

In the instant embodiment, the exposed end portions 24a, 26a, 38a, 38a of the leads 24, 26, 38, 38 are formed so as to be raised or protruded above the surface of the sensing layer 12 or the surface of the zirconia insulating layer 32, as illustrated in FIG. 9. This arrangement is preferable to assure sound contact of the exposed end portions 24a, 26a, 38a, 38a with the contact lugs 66 of the connectors 60 even if the sensing element 2 is deflected or flexed in the direction of width thereof. Although each of the first and second electrical terminal means 27 and 39 of the illustrated embodiment consists of the raised end portions 24a, 26a of the leads 24, 26, or of the raised end portions 38a, 38a of the leads 38, 38, it is also possible that the first and second electrical terminal means 27, 39 be constituted by electrical contacts (connected to the leads 24, 26, 38, 38) formed on base layers of a suitable thickness which are formed on the corresponding surfaces of the sensing layer 12 and zirconia insulating layer 32.

While the present invention has been described in its preferred embodiment for illustrative purpose, it is to be understood that the invention is not confined to the precise disclosure, and that many changes and modifications may be made therein.

For example, the sensing element 2 which, in the illustrated embodiment, is produced by lamination of plural layers of solid electrolyte material consisting substantially of zirconia ceramics, may be manufactured by printing such plural layers one on another. In this case, the green structure of the printed layers is fired into the sensing element. Although it is preferred to form the sensing element 2 of a solid electrolyte which consists substantially of zirconia ceramics, it is possible to use other solid electrolyte materials.

Further, the oxygen detecting portion 4 of the sensing element 2 may be formed substantially of an oxide semi-conductor such as titanium oxide whose electrical resistance is varied as a function of an oxygen concentration of a measurement gas such as an exhaust gas. In this instance, the oxygen sensor detects a variation in the electrical resistance of the detecting portion 4 which is caused by a variation in the oxygen partial pressure of the measurement gas.

Figure 10:
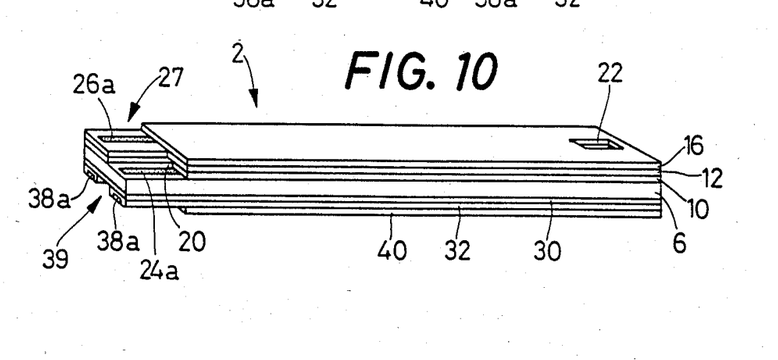
FIG. 10 is a perspective view corresponding to FIG. 2, illustrating an alternative form of the oxygen sensing element usable in the oxygen sensor of FIG. 1.

While the exposed end portions 24a and 26a of the leads 24, 26 or the exposed end portions 38a, 38a of the leads 38, 38, are disposed in the same plane perpendicular to the direction of thickness of the sensing element 2, it is possible that those two exposed end portions (electrical contacts) 24a and 26a, or 38a and 38a be disposed in different planes as illustrated in FIG. 10. In this case, the lead-wire holes 58 formed in the insulating member 44 are disposed so that they are aligned with the exposed end portions of the respective leads, so as to permit the connectors 60 to be brought into contact with the exposed end portions of the leads. If this arrangement is adopted, it is common that the sensing element 2 is manufactured by a suitable printing technique such as a screen printing.

In the illustrated embodiment of FIGS. 1-9, the first and second electrical terminal means 27, 39 at the second end portion of the sensing element 2 serve as a male connector or a plug which engages a female connector or a receptacle constituted by the connectors 60 disposed in the second insulating member 44. However, it is possible to reverse this arrangement, that is, to construct the first and second electrical terminal means 27, 39 in the form of a receptacle consisting of female electrical contacts, and to provide a plug consisting of male connectors within the second insulating member 44, so that the male connectors are inserted into the receptacle for contact with the female electrical contacts.

It will be obvious to those skilled in the art that various other changes, modifications and improvements are possible without departing from the scope of the invention defined in the appended claims.

What is claimed is:

1. An oxygen sensor including an elongate planar oxygen sensing element having a first longitudinal end and a second longitudinal end, wherein an oxygen detecting portion is adjacent to said first longitudinal end, said detecting portion being exposed to a measurement gas to determine an oxygen concentration of said measurement gas, said sensing element being electrically connected to at least one external device through at least one conductor member, wherein the improvement comprises:
   a protective covering having a first longitudinal end and a second longitudinal end, said protective covering accommodating therein said sensing element;
   a rubber plug having a first end and a second end, whereby said second end is press-fitted into said first longitudinal end of said protective covering, said at least one conductor member extending through said rubber plug;
   an electrical insulating member disposed between and retained by said second longitudinal end of said sensing element and said second end of said rubber plug;
   electrical terminal means formed on said sensing element, adjacent to said second longitudinal end thereof, said electrical terminal means including at least one pair of electrical contacts disposed in said electrical insulating member; and
   connector means disposed adjacent to said electrical terminal means, and including connectors which are electrically connected to said conductor members and are fixedly supported in said electrical insulating member, said connectors being held in direct electrical contact with said at least one pair of electrical contacts.

2. The oxygen sensor of claim 1, wherein said electrical terminal means of said sensing element consists of a plug, and said connector means consists of a receptacle into which said plug is inserted to achieve pressed contact between said at least one pair of electrical contacts and said connectors.

3. The oxygen sensor of claim 1, wherein said electrical terminal means of said sensing element consists of a receptacle, and said connector means consists of a plug which is inserted into said receptacle to achieve pressed contact between said connectors and at least one pair of electrical contacts.

4. The oxygen sensor of claim 1, wherein said at least one pair of electrical contacts consists of an output signal and an earth contact, said conductor members including said protective covering, said output signal contact being connected to said external device through a corresponding one of said connectors and through one of said conductor members, said earth contact being grounded through a corresponding one of said connectors and through said protective covering.

5. The oxygen sensor of claim 1, wherein said at least one pair of electrical contacts of said electrical terminal means comprises end portions having at least one pair of electrical leads formed on said sensing element, said end portions of the electrical leads being exposed adjacent to said second longitudinal end of the sensing element.

6. The oxygen sensor of claim 5, wherein said at least one pair of electrical leads comprises a pair of leads connected to a pair of electrodes disposed in said oxygen detecting portion of the sensing element, one of said pair of electrodes being exposed to said measurement gas.

7. The oxygen sensor of claim 6, wherein said conductor members comprise said protective covering, the exposed end portion of the electrical lead connected to said one electrode being grounded through a corresponding one of said connectors and through said protective covering.

8. The oxygen sensor of claim 6, wherein the exposed end portions of said pair of leads are formed on one of opposite surfaces of said sensing element perpendicular to the direction of thickness thereof.

9. The oxygen sensor of claim 5, wherein said sensing element comprises an electrical heater incorporated therein to heat said oxygen detecting portion thereof, said at least one pair of electrical leads comprising a pair of leads connected to said electrical heater to apply power thereto.

10. The oxygen sensor of claim 1, wherein said sensing element comprises an electrical heater incorporated therein to heat said oxygen detecting portion thereof.

11. The oxygen sensor of claim 1, wherein said at least one pair of electrical contacts are exposed adjacent to said second longitudinal end of said planar sensing element, each of said electrical contacts being raised above a surface of the planar sensing element.

12. The oxygen sensor of claim 11, further comprising an electrically insulating member in which said connectors are fixedly supported for electrical contact with said at least one pair of electrical contacts.

13. The oxygen sensor of claim 12, wherein an end portion of said sensing element on the side of said second longitudinal end thereof is inserted into said insulating member for electrical contact of said electrical contacts with said connectors supported in said insulating member.

14. Th oxygen sensor of claim 12, wherein each of said connectors includes a contact lug which is resiliently held in pressed contact with a corresponding one of said electrical contacts.

15. The oxygen sensor of claim 11, wherein said at least one pair of electrical contacts comprises a first pair of electrical contacts electrically connected to a pair of electrodes disposed in said oxygen detecting portion of the sensing element, and a second pair of electrical contacts electrically connected to an electrical heater incorporated in said sensing element to heat said oxygen detecting portion.

16. The oxygen sensor of claim 15, wherein said first pair of electrical contacts consists of end portions of electrical leads extending from each of said pair of electrodes, and said second pair of electrical contacts consists of end portions of electrical leads extending from said electrical heater, each of said end portions of the electrical leads being raised above a surface of the sensing element.

17. The oxygen sensor of claim 16, wherein the end portions of said electrical leads of said pair of electrodes are found on a first surface of opposite surfaces of the sensing element perpendicular to the direction of thickness thereof, and the end portions of said electrical leads of said electrical heater are formed on a second surface of the opposite surfaces of the sensing element.

18. The oxygen sensor of claim 16, wherein the end portions of said electrical leads of said pair of electrodes are formed substantially in the same plane perpendicular to the direction of thickness of said sensing element.

19. The oxygen sensor of claim 16, wherein the end portions of said electrical leads of said electrical heater are formed substantially in the same plane perpendicular to the direction of thickness of said sensing element.

20. The oxygen sensor of claim 16, wherein the end portions of said electrical leads of said pair of electrodes are formed in different planes perpendicular to the direction of thickness of the sensing element.

21. The oxygen sensor of claim 1, wherein said oxygen detecting portion of the sensing element comprises a solid electrolyte material consisting essentially of zirconia ceramics, and is operated to determine the oxygen concentration of said measurement gas according to the principle of an oxygen concentration cell.

22. The oxygen sensor of claim 1, wherein said oxygen detecting portion of the sensing element comprises an oxide semiconductor, having an electrical resistance which varies as a function of an oxygen partial pressure of said measurement gas.

* * * * *